United States Patent [19]
Liebl et al.

[11] Patent Number: 4,965,197
[45] Date of Patent: Oct. 23, 1990

[54] CORYNEFORM EXPRESSION AND SECRETION SYSTEM

[75] Inventors: Wolfgang Liebl, Eching, Fed. Rep. of Germany; Anthony J. Sinskey, Boston, Mass.

[73] Assignee: Massachusetts Institute of Technology, Cambridge, Mass.

[21] Appl. No.: 446,306

[22] Filed: Dec. 5, 1989

Related U.S. Application Data

[63] Continuation of Ser. No. 61,883, Jun. 12, 1987, abandoned.

[51] Int. Cl.$^5$ .................. C12P 21/00; C12N 15/00; C12N 1/20
[52] U.S. Cl. .................. 435/69.8; 435/172.3; 435/252.3; 435/252.32; 435/320; 935/29; 935/48; 935/72
[58] Field of Search ............... 435/252.32, 172.3, 320, 435/69.8; 935/48, 72

[56] References Cited

U.S. PATENT DOCUMENTS

| | | | |
|---|---|---|---|
| 4,601,983 | 7/1986 | Nakamori et al. | 435/115 |
| 4,649,119 | 3/1987 | Sinskey et al. | 435/317 |
| 4,758,512 | 7/1988 | Goldberg et al. | 435/68 |
| 4,778,762 | 10/1988 | Miwa et al. | 435/320 |
| 4,830,962 | 5/1989 | Gelfand et al. | 435/68 |

OTHER PUBLICATIONS

Fahnestock et al., *Applied and Environmental Microbiology* 53: 379–384, 1987 (Feb.).
Follettie et al., *J. Bacteriology* 167: 695–702, 1986 (Aug.).
Yoshihama et al., *J. Bacteriology* 162: 591–597, 1985.

*Primary Examiner*—Thomas D. Mays
*Attorney, Agent, or Firm*—Kilpatrick & Cody

[57] ABSTRACT

A coryneform expression and secretion system for homologous and heterologous genes consisting of the host, nucleotide sequences encoding a protein of interest, signals for expression and, optionally, targeting signals which direct membrane anchoring and for secretion and processing of the expressed protein. Regulatory signals may be utilized to control the rate and extent of expression and secretion. The system may further include compounds such as ionophores for altering the membrane transport of the host. The host itself may be mutated to alter transport, for example, by decreasing the mycolic acid content of Corynebacteria species.

The preferred host is a Corynebacterium although other coryneforms deficient in extracellular protease production may also be used. *C. glutamicum* is used as a model organism for the secretion system. This Gram positive, non-pathogenic bacteria can efficiently utilize heterologous expression and secretion signals originating from a variety of both Gram negative and Gram positive bacteria to provide the basis for the overproduction and secretion of cloned gene products in a given Corynebacterium host, as demonstrated by the expression and secretion by *C. glutamicum* of a lipase encoded by a gene from *S. hyicus* and a thermonuclease encoded by a gene from *S. aureus*.

25 Claims, 2 Drawing Sheets

CORYNEFORM EXPRESSION AND SECRETION SYSTEM

This is a continuation of Ser. No. 061,883, filed June 12, 1987, by Wolfgang Liebl and Anthony J. Sinskey, now abandoned.

BACKGROUND OF THE INVENTION

The present invention is in the area of improved procaryotic expression systems and, in particular, a Coryneform host system for the expression and excretion of gene products.

Coryneform bacteria are a taxonomically ill-defined group of Gram positive bacteria originally related by unique morphological features. These microorganisms occupy a wide variety of ecological niches and display an even broader array of interesting and useful properties. With the advent of systematic chemical analysis, there is considerable evidence indicating that the genus *Corynebacterium* is closely related to *Mycobacterium* and *Norcardia*. Included in the genus *Corynebacterium* are medically important species such as *C. dipthereiae*, animal pathogens such as *C. renale*, plant pathogens and diverse saprophytic, aerobic coryneform bacteria. The saprophytic coryneform bacteria are widely distributed in nature and include not only Corynebacterium species but also other bacteria including Arthrobacter, Brevibacterium, Cellulomonas, Microbacterium and Curtobacterium. The coryneform group thus represents an important source of enzymes, primary metabolites, and genetic material.

When cloning heterologous proteins for purification, it is often desirable to have the gene product hyperproduced and/or secreted by the host cells. The major advantages of secretion over intracellular accumulation of recombinant proteins are an increase in yield and the facilitation of product purification. Translocation of proteins into or through membranes is an essential feature of prokaryotic and eukaryotic cells. Proteins that are partially or fully integrated into membranes, proteins that are associated or covalently bound to cell walls, or proteins that are secreted, must cross the cytoplasmic membrane.

Although initial investigations on protein export have beer carried out with eukaryotic systems, there is an increasing interest in the mechanism and genetics of bacterial protein export. Benson et al., Cell 32, 1325-1335 (1985); D. Oliver, *Ann.Rev.Microbirl.* 39,615-648 (1985); Randall and Hardy, *Microbiol.Rev.* 48, 290-298 (1984); and Pugsley and Schwartz, *FEMS Microbiol.Rev.* 48,290-298 (1985), have recently reviewed this area. The Gram negative *E. coli* is the best-studied species among the prokaryotes. The most advanced experimental techniques have been tailored especially to fit the *E. coli* system. Despite the fact that the Gram positive cell well has a simpler structure than its Gram negative counterpart, that Gram positive organisms are often very efficient in secreting proteins to the culture medium as compared with Gram negative organisms which normally cannot transport proteins beyond the outer membrane of their cell envelope, and that a vast number of extracellular proteins of Gram positive bacteria have been isolated and examined, including most bacterial enzymes of commercial importance, the use of these organisms for basic investigations of protein export has been limited.

Most exported proteins, contrary to the majority of proteins localized in the cytoplasmic membrane, are synthesized as precursors with an N-terminal peptide extension (signal peptide) that is cleaved off in the course of translocation. Many of the bacterial and eukaryotic signal sequences that have been studied share striking structural similarities and are in fact interchangeable, as reported by several investigators. For example, the *E. coli* leader peptidase precisely recognizes and cleaves eukaryotic precursors.

Protein fusion experiments have demonstrated that a signal sequence alone is generally insufficient for the proper export of proteins. Several other types of targeting signals in addition to signal peptides have been identified. The most complex situation is found in eukaryotic cells where proteins must be directed to different subcellular compartments: endoplasmic reticulum, mitochondria, or chloroplasts. Additional information in the body of the mature protein may also be necessary. For example, posttranslational modification may contribute to the final localization of a protein, as seen with Gram negative lipoproteins and Gram positive lipopenicillinases.

Unfortunately, at this time, a good Gram positive cloning host has not been identified. The classic Gram positive cloning host, *B. subtilis*, secretes extracellular proteases which attack heterologous proteins expressed in this organism, as reported by Ulmanen et al., *J.Bacteriol.* 162,176-182 (1985) and Doi et al., *Trends in Biotech.* 232-235 (1986). Consequently, there is a clear need for alternative Gram positive host organisms.

Protein secretion by coryneform bacteria has not been investigated, other than the secretion of diphtheria toxin by the pathogenic *C. diptheriae* upon infection with certain lysogenic tox+ phages, reported by Pappenheimer, *Ann.Rev.Biochem.* 46,69-94 (1977) and Neville and Hudson, *Ann.Rev.Biochem.* 55,195-224 (1986). Even reports of the cloning in *Corynebacterium* hosts of the genes for two proteins which are normally exported in their native hosts, beta-lactamase from *E. coli* and alpha-amylase from *Bacillus amyloliquefaciens*, do not disclose whether or not these heterologous proteins were secreted.

It is therefore an object of the present invention to provide a Gram positive bacterial expression and secretion system.

It is another object of the present invention to characterize gene expression (replication, conjugal transfer and plasmid biology), in the Gram positive bacterial expression system.

It is yet another object of the present invention to further elucidate the genomic organization and structure of the Gram positive host, including the isolation and characterization of high efficiency and regulatable promoters.

SUMMARY OF THE INVENTION

A Coryneform expression and secretion system for cloned gene sequences consisting of the host nucleotide sequences encoding a protein of interest, signals for expression and, optionally, targeting signals which direct membrane anchoring and for secretion and processing of the expressed protein. In the preferred embodiment of the system for the expression and secretion of homologous and heterologous sequences, a *Corynebacteria* is selected as the host. The protein-encoding gene, transcriptional and translational start signals and a sequence coding for a secretion signal peptide are usually provided in a secretion vector, optionally including an inducible promoter. Regulatory signals may be utilized to control the rate and extent of expression and secretion. The system may further include compounds such as ionophores for altering the membrane transport of the host. The host itself may be mutated to alter transport, for example, by decreasing the mycolic acid content.

*C. glutamicum* is used as a model organism for the secretion system. This is a Gram positive, non-pathogenic bacterium which can efficiently utilize heterologous expression and secretion signals originating from a variety of both Gram negative and Gram positive bacteria to provide the basis for the overproduction and secretion of cloned gene products in a given *Corynebacterium* host.

The overexpression and secretion of foreign cloned genes in this system, and the exceptional suitability of *Corynebacterium* as a host organism for the production and secretion of foreign gene products, is demonstrated by the expression and secretion by *C. glutamicum* of a lipase encoded by a gene from *S. hyicus* and a thermonuclease encoded by a gene from *S. aureus*.

DETAILED DESCRIPTION OF THE INVENTION

Figure 1:
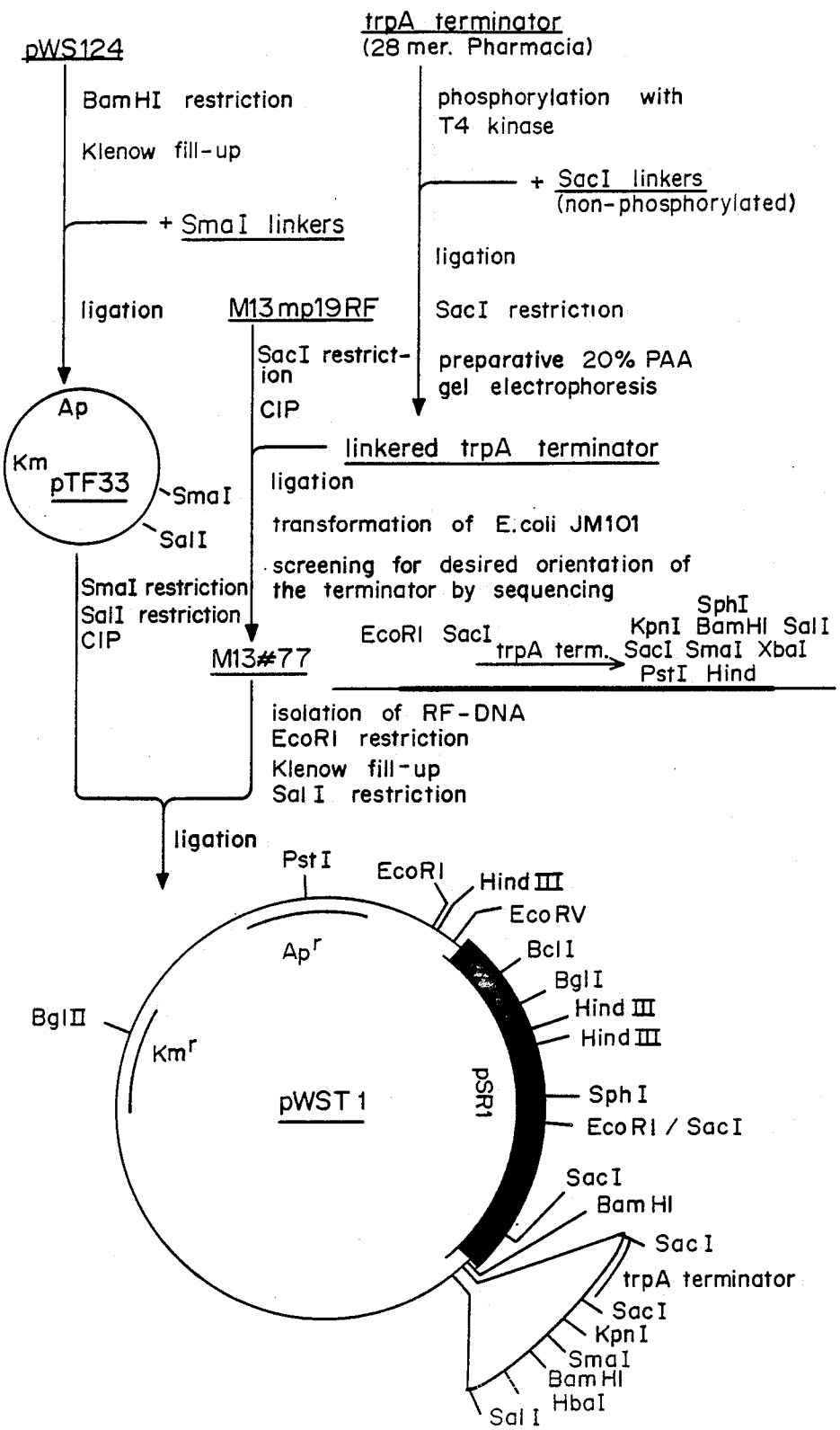
FIG. 1 is the construction of plasmid pWST1. A SmaI restriction site was introduced into the BamHI site of pWS124 on a synthetic oligonucleotide to create pTF33. The trpA terminator, from *E. coli*, was obtained as a 28 bp oligonucleotide and ligated to SacI linkers and cloned into M13 mp19 and screened by sequencing. Replicative form DNA of M13#77 was isolated and the terminator introduced into the SmaI-SacI region of pTF33 as a blunt ended EcoRI-SacI fragment to create pWST1.

The present invention is a Coryneform expression and secretion system, and methods for its manufacture, demonstrated using *C. glutamicum* as a model organism for this group.

As discussed in the Background of the Invention, the coryneform group of bacteria encompasses a number of diverse, Gram positive organisms, including Corynebacterium, Arthrobacteria, Nocardia, Mycobacterium, Cellulomonas, Microbacterium and Curtobacterium. To be useful in the present invention, the bacterial lost must be deficient in protease production, especially extracellular proteases. Preferably, the host should be amenable to large scale fermentation conditions, i.e., have simple nutritional requirements; grow within a wide range of temperatures, between 20 and 65° C.; of food grade or being generally regarded as safe, such as *Brevibacterium lactcfermentum, Lactobaccillus* species and *Streptococci;* non-spore forming, unlike most strains of *Bacillus;* transformable; and genetically stable, as opposed to many *Bacillus* and *Streptomyces* strain. *Corynebacteria* strains and particularly *C. glutamicum*, are preferred at this time.

In the past, it has not been possible to directly address questions of gene organization, structure and regulation of *Corynebacterium* at the molecular level due to deficiencies in the genetic tools that were available, even though *Corynebacterium* has long occupied a central role in the manufacture of a variety of primary metabolites including L-amino acids, nucleotides and organic acids by conventional fermentation. Several features of *C. glutamicum* make it especially desirable for extensive genetic studies: *C. glutamicum* is a nonpathogenic, food-grade microorganism, and the biochemistry and enzymology of *C. glutamicum* biosynthetic pathways have been extensively characterized.

As detailed below, there are a number of methods and variables to consider in the construction of an expression system using *Corynebacterium* as the host. Depending on the protein to expressed, the degree of regulation and quantity of expression desired, and whether or not the protein is to be secreted and/or targeted, the system can consist of as little as the host and an expression vector containing transcription and translation signals and the gene to be expressed. For the expressed protein to be secreted, the vector must further include targeting signals such as secretion signals, processing signals, ant membrane anchoring signals. For control of the :ate and extent of expression, the promotor may be placed under the control of a repressor or stimulatory protein. The expression/ secretion system as a whole may also be modified by point mutations or deletions in any of the sequences discussed above, by the addition of membrane transport altering substances, or by mutations in the host affecting cell components such as the mycolic acid content of the cell wall.

The first consideration is to determine the protein to be expressed and to isolate a sequence encoding some or all of the protein. Methods for isolation of protein-encoding sequences are known to those skilled in the art of genetic engineering. Examples of the isolation and characterization of genes from *C. glutamicum* are provided.

The second consideration is the selection of an appropriate vector. A useful vector is pWST1 which contains the *E. coli* trpA transcription terminator obtained from Pharmacia Fine Chemicals, Piscataway, New Jersey, immediately upstream of a polylinker cloning site. pWST1 is shown in FIG. 1 and has particular utility in investigating promoter structure and function by eliminating read-through transcription from upstream promoters located within the cloning vector. Further examples of suitable vectors for use in *Corynebacterium* are described by U.S. Pat. No. 4,649,119 to Sinskey et al. Other useful vectors, and methods for inserting the gene of interest into the vector, will be apparent to those skilled in the art.

Once the nucleotide sequence and the vector have been selected, sequences for the expression, regulation of expression, and post-translational characteristics of the expressed protein can be isolated and inserted into the vector. A number of promoters are useful in the present invention, including heterologous expression signals originating from a variety of both Gram negative and Gram positive bacteria including Escherichia, Bacillus, Staphylococcus and Streptococcus species. Of course, expression signals present in *Corynebacterium* are also useful. Indeed, an important feature of the present invention is not only the expression and secretion of gene products, but utilization of either homologous or heterologous gene sequences by the host.

An important element of the mechanism by which *C. glutamicum* mediates gene expression is through promoter structure and the structure/function relationships. The promotors of naturally occurring genes can be determined by S1 nuclease mapping, described by Berk and Sharp in *Cell,* 12, 721(1977) using comparisons between known promoter sequences and the sequence which is being characterized. Identification of the transcription initiation sites and the alignment of upstream sequences can be used to identify consensus sequences. Deletion analysis of the isolated gene can also be used to confirm the promoter identification and to allow promoter replacement. In vitro generated deletions can be constructed using restriction enzymes or the exonuclease BAL31. The insertion of linkers facilitates subsequent cloning and sequencing. Restriction enzymes and linkers are commercially available from sources including Boehringer-Mannheim Biochemicals, Indianapolis, IN, and New England Biolabs Inc., Beverly, MA.

In some situations, it may be desirable to bring expression of a gene under control of a specific effector or repressor. In this case, either a regulatable promoter could be inserted prior to the gene, or the gene fused to the 3'end of a gene under the transcriptional control of a particular metalolite such as phenylalanine. Alternatively, an inducible promoter that allows product formation to be switched on during the appropriate growth phase, for example, as described Ghrayeb et al., *EMBO J.* 3,2437-2442 (1984), or mutant high copY vectors that allow overproduction of proteins could be used.

Secretion vectors are a specialized form of expression vectors and have to be specifically designed for each cloning system. They must carry efficient transcriptional and translational start signals as well as sequences coding for the N-terminal portion (at least the signal peptide) of a secreted protein. Secretion vectors have been constructed for various microbial cloning hosts, including *E. coli,* as reported by Takahara et al., *J.Biol. Chem.* 260, 2670-2674 (1985), *B. subtilis,* as reported by Palva et al., *Proc.Natl.Acad.Sci.USA* 79,5582-5586 (1982); Ohmura et al., *J.Biochem.* 95, 98-93 (1983); and Kovacevic et al., *J.Bact.* 162,521-528 (1985), staphylococci, as reported by Nilsson et al., *Nucl. Acids Res.* 13,1151-1162 (1985), and Liebl and Gotz, *Mol.Gen.-Genet.* 204,166-173 (1986), and yeast, reported by Smith et al., *Science* 229,1219-1224 (1985).

A secretion signal sequence that functions in *C. glutamicum* can be selected by screening for expression of homologous or heterologous exoprotein genes in *C. glutamicum* and then used to form the basis of a secretion vector. The efficiency of this system can be tested by in-frame fusions of foreign genes, such as the structural gene for *E. coli* beta-lactamase devoid of its own expression/secretion signals, to the signal sequence. Expression of the gene fusion can be regulated either by the native promoter of the chosen exoprotein gene or by a homologous *Corynebacterium* promoter isolated in promoter search experiments. The amount and integrity of foreign protein released to the growth medium upon transformation of *C. glutamicum* with the gene fusion demonstrates the capacity of this host organism to produce and secrete recombinant proteins.

Additionally, a sequence encoding an affinity tail, such as the IgG binding domain of protein A, could be inserted into the vector following the gene to be expressed to facilitate purification of the secreted product (Nilsson et al., *Nucl. Acids Res.* 13, 1151-1162, (1985)).

An element to be considered in protein secretion by *C. glutamicum* is the determination and characterization of targeting sequences which direct secretion membrane anchoring and post-translational processing of protein in *C. glutamicum.* One source of targeting signals are extracellular enzymes such as the lipase produced by *P. acnes.* Cloning of this lipase gene provides an exoprotein encoding gene from a species which is relatively closely related to *C. glutamicum.* Expression of the gene is detected by the presence of lipase activity. Staphylococci produce a number of extracellular proteins, some of which are bound to the cell wall of their native host. Examples of extracellular proteins produced by *S. aureus* are thermonuclease and protein A, both structurally and functionally well characterized proteins. The nucleotide sequences of the genes, as well as the N-terminal amino acid sequences of the mature proteins, are known. These genes can be placed under the transcriptional control of strong host promoters on an expression vector for study, as well as placed under the control of their own native promoters. Analysis of the expression and localization of these proteins provides information on the recognition of heterologous targeting signals in coryneforms.

The energy requirement for secretion by *C. glutamicum* is another factor which can be characterized and altered as desired to modify secretion of proteins from the *corynebacterium* expression system. Transfer of proteins to the endoplasmic reticulum of eukaryotic cells is coupled to translation (cotranslational) and is driven by a mechanism that depends on the chain elongation process. Although some *E. coli* proteins (AMP C protein) exhibit complete cotranslational processing, others such as beta-lactamase and M13 code protein are synthetized to completion before export and processing are initiated. Most exported *E. coli* proteins show both cotranslational and post-translational processing. Translocation and processing do not initiate until at least 80% of the polypeptide chain is complete. Protein export in *E. coli* depends on the total proton motive force (PMF), although the mechanism of the coupling membrane energy to transmembrane protein transport is unknown. The same coupling was found for the secretion of alpha-amylase in *B. amyloliquefaciens.* It is therefore expected that the same methods may be used to alter protein secretion in *corynebacterium,* in addition to modification by genetic engineering.

*C. glutamicum* clones expressing exoprotein genes can be used to investigate the energy requirements of *corynebacterium,* and possible ways to alter the requirements and the effect of these alterations on protein expression and secretion. For example, the effect of varying the concentration of the ionophores carbonylcyanide M-chlorophenyl hydrazone (CCCP) and valinomycin in combination with K+ on secretion can be determined. Inhibition of export and accumulation of cell-associated precursor molecules in the presence of these ionophores which reduce the PMF indicate the requirement of an energized membrane for translocation. One must take into consideration, however, that the effectiveness of these ionophores may be altered by the lipid-rich cell wall of the *corynebacterium.*

The mycolic acid layer of the corynebacterial cell wall may exert an effect on protein secretion. Production of mycolic acids (3-hydroxy-2-alkyl fatty acids) is a unique property of *Corynebacterium, Mycobacterium, Nocardia* and related taxa. The carbon chain link is taxon specific and is widely used in clarifying the taxonomy of the actinomycetes. Mycolic acids, arabinogalactan and peptidoglycan are interconnected and comprise the three main components of the cell walls of these bacteria. The function of the lipid outer cell wall layer in vivo is uncertain. It is likely that it plays a role in the interactions between the bacterium and its surroundings, for example, as a semipermeable membrane and in the selective uptake/ release transport of compounds or compartmentation of cerain proteins.

In order to both determine the effect of cell wall mycolic acids on protein secretion and to decrease the effect when it is so desired, mutants defective in mycolic acid synthesis are generated using mutation techniques known to those skilled in reduced mycolic acid levels since totally deficient mutants are probably lethal. Deficient mutants can be screened for by staining with basic fuchsin in phenol water. Loss of the lipid rich outer coat decreases the retention of the stain.

The following examples demonstrate the isolation and characterization of native genes from *C. glutamicum*, the isolation and utilization of secretion signals for the export of the cloned gene products, and the overproduction of the cloned gene products in a Corynebacterium host.

Isolation and Identification of Corynebacterium Genes and Their Promoters

Genes encoding enzymes in various biosynthetic pathways, along with expression signals, can be isolated from a genomic library by complementation of an auxotrophic strains. Complementation analysis indicates that many *C. glutamicum* genes can be isolated by the heterologous complementation of *E. coli* auxotrophs followed by hybridization to elucidate the genomic organization of the isolated gene. Promoters for the gene of interest are then characterized. One technique is to use S1 nuclease mapping to identify the transcription start site of the gene. Comparison between known promoter sequences can be used to identify functionally important nucleotides. Replacement of promoters can then be achieved using in vitro generated deletions.

The functional activity of the isolated gene and its promoters are tested by insertion of the recombinant plasmid into the expression host. Where a regulated gene is isolated, control of encoded activity by an effector proves that both the structural and regulatory sequences have been cloned. Northern hybridization analysis can be used to quantify the amount of gene specific message isolated from *Corynebacteria* grown in minimal medium with and without effector supplementation.

The mechanism of regulation of a particular system can be determined and then modified using one or more of the following methods. The involvement of a trans activity component in effector mediated repression is determined by cloning DNA fragments containing the proposed operator region, but not a functional gene, and introducing the cloned fragments into wild type *C. glutamicum*. Cloning of a larger portion of the operator region onto a multicopy plasmid could potentially influence transcription of the chromosomal encoded gene by titration of a repressor. The in vitro construction of point mutations and specific deletions which modify the operator region can also be used. Identification and modification of operator sequences could also enable in vitro isolation of repressor proteins for indirect, as well as direct, manipulation of expression.

Expression and Secretion of Non-Corynebacterium Genes in Corynebacterium

Although Staphylococci are not closely related to *Corynebacterium*, several *Staphylococcus* genes have been expressed in *C. glutamicum*. The lipase gene from *Staphylococcus hyicus*, described by Gotz et al., *Nucl.Acids.Res.* 13,5895–5906 (1985), and the thermonuclease gene from *S. aureus*, described by Shortle, *Gene* 22,181–189 (1983), were cloned into *C. glutamicum*.

Both the gene encoding nuclease production from *S. aureus* and the gene encoding lipase production from *S. hyicus* were readily expressed by *C. glutamicum*. The gene product was secreted into the culture medium. The cloned lipase gene is located downstream of the transcriptional terminator in the *E. coli/C. glutamicum* shuttle vector pWST1. It is presumed that in this situation the lipase gene is expressed via its native transcriptional promoter since the relative orientation of the gene in pWST1 does not influence its expression. *C. glutamicum* transformants harboring the lipase gene were analyzed by SDS polyacrylamide gel electrophoresis and an activity staining procedure (Gotz et al., 1985) which revealed a protein band at 45,000 Da with lipase activity.

Isolation and Utilization of Secretion Signals from Corynebacterium

Several proteins are released into the culture medium by the wild type strain of *C. glutamicum*. The gene coding for one such protein, DNAse, was cloned. Upon reintroduction into *C. glutamicum*, this gene results in the overproduction and secretion of active DNAse. The cloned gene also provides a source of homologous expression and secretion signals useful in the construction of expression/ secretion vectors for *C. glutamicum*.

Figure 2:
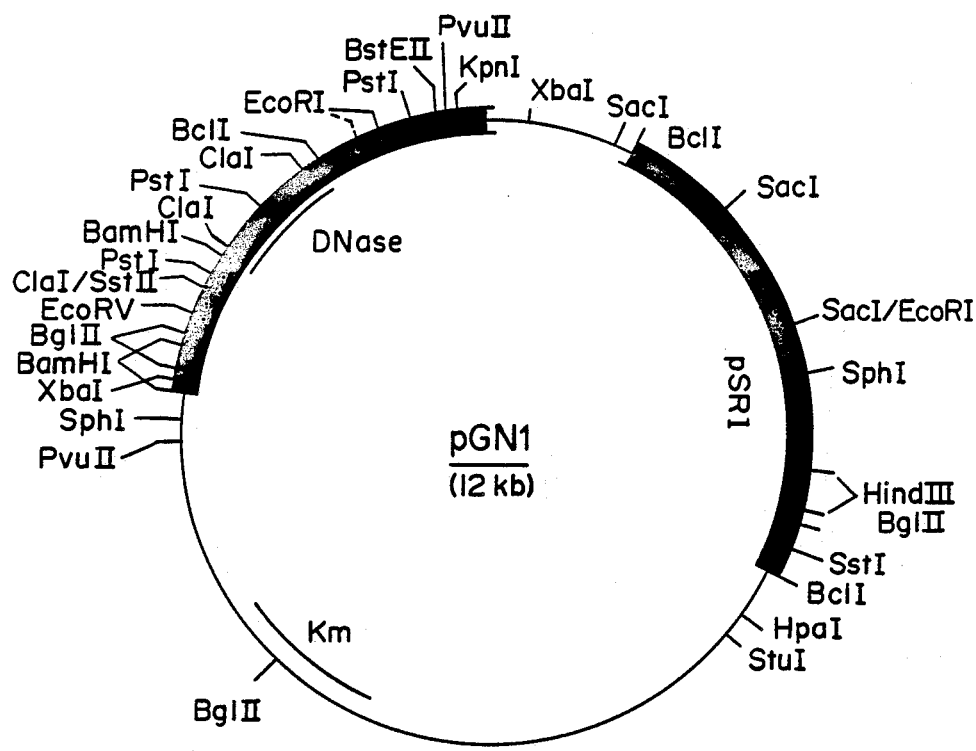
FIG. 2 is the restriction endonuclease map of pGN1. The *C. glutamicum* DNase gene was shown to reside on a 1.1 kb BamHI-BclI fragment within the 2.7 kb chromosomal DNA insert.

The gene was isolated and utilized as follows. Chromosomal DNA from *C. glutamicum* was partially digested with MtoI and 6 to 12 kb large fragments were ligated into the BamHI site of pHY416, described by Yoshihama et al., *J.Bacteriol.* 162,591–597 (1985), and Follettie and Sinskey, *J.Bacteriol.* 67,695–702 (1986). After transformation of the recombinant plasmids into *C. glutamicum* AS101 (his, Rif$^r$), 1,500 Km$^r$ clones were screened on DNase agar plates (Oxoid USA Inc., Columbia, MD). Two clones showed increased DNase activity, both of which were found to contain the same 2.7 kb chromosomal DNA fragment in their respective plasmids. The restriction endonuclease map of one of these plasmids, designated pGN1, is shown in FIG. 2. Deletion derivatives of pGN1 which were generated by BamHI or BclI digestion and religation (pGNBam4 and pGNBc13, respectively) still conferred to *C. glutamicum* the DNase overproduction phenotype, indicating the location of the DNase gene in pGN1 to be on a 1.1 kb BamHI-BclI fragment. The nucleotide sequence of the 1.2 kb BamHI-EcoRI chromosomal DNA fragment carrying the corynebacterial DNase gene can be determined using techniques and equipment available to those skilled in the art.

This example appears to be the first case of the cloning and investigation of a homologous extracellular protein from *C. glutamicum*. It is useful in defining the structure of expression and secretion signals on the DNA and protein level and is therefore important for the future construction of secretion vectors for this cloning host.

Modifications and variations of the present invention, a coryneform expression system for cloned genes from *Corynebacterium* or foreign sources with the additional feature that the encoded protein is secreted from the host without undergoing extensive proteolytic degradation, will be obvious to those skilled in the art of genetic engineering from the foregoing detailed description. Such modifications and variations are intended to come within the scope of the appended claims.

We claim:

1. A Gram positive bacterial expression and secretion system comprising:
   an isolated host Corynebacterium which does not produce extracellular proteases; and
   a secretion vector containing a first DNA sequence which promotes and regulates the expression in said Corynebacterium host a second DNA sequence that encodes a peptide or polypeptide and wherein said peptide or polypeptide does not naturally occur in said Corynebacterium host and a third DNA sequence inserted between said first and said second DNA sequences and wherein said third DNA sequence encodes for the secretion of said peptide or polypeptide from said Corynebacterium host.

2. The secretion system of claim 1 wherein said Corynebacterium is also non-spore forming, food grade, and grows at a temperature between 20° C. and 65° C.

3. The secretion system of claim 1 wherein said Corynebacterium is *Corynebacterium glutamicum*.

4. The secretion system of claim 1 wherein said expression sequences include a transcriptional start sequence and a translational start sequence.

5. The secretion system of claim 1 wherein said expression DNA sequences promoting and regulating include a termination sequence.

6. The secretion system of claim 1 wherein said DNA sequence promoting and regulating expression sequences is regulatable by the presence of a molecule not encoded by sequences encoded by the vector.

7. The secretion system of claim 1 wherein said expression DNA sequences promoting and regulating signals are isolated from non-Corynebacterium bacterial species.

8. The secretion system of claim 7 wherein said expression DNA sequences promoting and regulating signals are derived from bacteria selected from the group consisting of *Escherichia, Staphylococus, Streptococcus* and *Bacillus*.

9. The secretion system of claim 1 comprising nucleotide sequences selected from the group consisting of sequences directing membrane anchoring, in Corynebacterium.

10. The secretion system of claim 1 wherein said sequences are derived from a gene selected from the group consisting of the genes encoding lipase in *P. acnes*, lipase in *Staphylococci*, thermonuclease in *S. aureus* and protein A in *S. aureus*.

11. The secretion system of claim 1 wherein said sequence are isolated from the group consisting of Gram negative bacteria, Gram positive bacteria, and eukaryotic cells.

12. The secretion system of claim 1 further comprising a compound increasing or decreasing the proton motive force of the Corynebacterium cell membrane in an amount altering the translocation and post-translation processing of the peptide encoded by the second DNA sequence.

13. The secretion system of claim 12 wherein said compound is an ionophore.

14. The secretion system of claim 1 wherein the Corynebacterium does not produce mycolic acid.

15. A method for expressing and secreting cloned nucleotide sequences comprising:
   providing a host Corynebacterium which does not produce extracellular proteases; and
   a secretion vector containing a first DNA sequence which promotes and regulates the expression in said Corynebacterium host a second DNA sequence that encodes a peptide or polypeptide and wherein said peptide or polypeptide does not naturally occur in said Corynebacterium host and a third DNA sequence inserted between said first and said second DNA sequences and wherein said third DNA sequence encodes for the secretion of said peptide or polypeptide from said Corynebacterium host;
   inserting the vector into the Corynebacterium host and culturing the host under conditions wherein the peptide encoding sequences are expressed and the peptide is secreted by the host into the medium.

16. The method of claim 15 wherein said Corynebacterium host bacteria is also non-spore forming, food grade, and grows at a temperature between 20° C. and 65° C.

17. The method of claim 15 wherein the sequences for expression includes transcription and translation start sequences.

18. The method of claim 15 wherein the sequences for expression include a termination sequence.

19. The method of claim 15 further comprising providing sequences for the regulation of expression of said cloned nucleotide sequences.

20. The method of claim 15 further comprising providing nucleotide sequences selected from the group consisting of sequences encoding membrane anchoring peptides in Corynebacterium.

21. The method of claim 20 wherein said Corynebacterium further comprising selecting said nucleotide sequences from the genes encoding lipase in *P. acnes*, lipase in *Staphylococci*, thermonuclease in *S. aureus*, and protein A in *Staphylococci*.

22. The method of claim 20 further comprising selecting said sequences from sequences isolated from the group consisting of Gram negative bacteria, Gram positive bacteria, and eukaryotic cells.

23. The method of claim 15 further comprising providing a compound increasing or decreasing the proton motive force of the Corynebacterium cell membrane in an amount altering the translocation and post-translation processing of the peptide encoded by the second DNA sequence.

24. The method of claim 23 wherein said compound is an ionophore.

25. The method of claim 23 further comprising selecting a Corynebacterium which does not produce mycolic acid.

* * * * *